US011219571B2

United States Patent
Sato et al.

(10) Patent No.: US 11,219,571 B2
(45) Date of Patent: Jan. 11, 2022

(54) DENTAL INSTRUMENT HANGER (71) Applicant: THE YOSHIDA DENTAL MFG. CO., LTD., Tokyo (JP)

(72) Inventors: Takafumi Sato, Tokyo (JP); Yoshiki Gotani, Tokyo (JP); Keiichi Kudo, Tokyo (JP)

(73) Assignee: The Yoshida Dental Mfg. Co., Ltd.

( * ) Notice: Subject to any disclaimer, the term of this patent is extended or adjusted under 35 U.S.C. 154(b) by 459 days.

(21) Appl. No.: 16/083,083

(22) PCT Filed: Apr. 24, 2017

(86) PCT No.: PCT/JP2017/016220
§ 371 (c)(1),
(2) Date: Sep. 7, 2018

(87) PCT Pub. No.: WO2017/208678
PCT Pub. Date: Dec. 7, 2017

(65) Prior Publication Data
US 2019/0070055 A1    Mar. 7, 2019

(30) Foreign Application Priority Data

Jun. 1, 2016    (JP) .............................. JP2016-110411

(51) Int. Cl.
A61G 15/16    (2006.01)
A61C 19/00    (2006.01)
(Continued)

(52) U.S. Cl.
CPC .............. A61G 15/16 (2013.01); A61B 90/90 (2016.02); A61B 90/98 (2016.02); A61C 1/0015 (2013.01);
(Continued)

(58) Field of Classification Search
CPC ...... A61G 15/16; A61C 2204/005–007; A61C 1/0015; A61C 19/00; A61B 90/90; A61B 90/98
See application file for complete search history.

(56) References Cited

U.S. PATENT DOCUMENTS

2004/0209223 A1* 10/2004 Beier ................. A61B 17/1626
433/99
2008/0221564 A1* 9/2008 Rouiller .................... A61C 5/42
606/40
(Continued)

FOREIGN PATENT DOCUMENTS

DE    102007008366 A1 *  8/2008 ............. A61G 15/16
EP       2327370 A2 *  6/2011 ............. A61C 1/185
(Continued)

OTHER PUBLICATIONS

International Search Report issued in corresponding international application No. PCT/JP2017/016220, dated Jul. 25, 2017. (with English language translation).
(Continued)

Primary Examiner — Jacqueline T Johanas
Assistant Examiner — Shannel Nicole Belk
(74) Attorney, Agent, or Firm — Day Pitney LLP; Valeriya Svystun (57) ABSTRACT A dental instrument hanger has the body of a reader/writer, or an antenna connected to the body, arranged in a hanger unit so as to read identification information from a wireless tag, in a state that an instrument having the wireless tag preliminarily attached thereto is placed in the hanger unit. The hanger includes: an identification information storage that stores the read identification information in a database; a reading history detector that, in response to a driving instruction having been inputted, detects the latest reading history and a reading history read before the instrument
(Continued)

displaced from the hanger unit has been displaced with reference to said storage; an identification information specifier that determines a difference between the two reading histories to specify a wireless tag attached to the instrument which has been instructed to drive; and a usage information generator that generates usage information of the instrument.

20 Claims, 7 Drawing Sheets

(51) Int. Cl.
 *A61B 90/98* (2016.01)
 *A61C 1/00* (2006.01)
 *A61B 90/90* (2016.01)
(52) U.S. Cl.
 CPC ........ *A61C 19/00* (2013.01); *A61C 2204/005* (2013.01)

(56) References Cited

U.S. PATENT DOCUMENTS

| 2010/0281636 | A1* | 11/2010 | Ortins | A46B 15/001 15/4 |
| 2018/0092712 | A1* | 4/2018 | Bosisio | A61B 5/0534 |
| 2018/0256287 | A1* | 9/2018 | Bosisio | A61C 1/148 |
| 2018/0353275 | A1* | 12/2018 | St. Louis | A61C 1/181 |

FOREIGN PATENT DOCUMENTS

| JP | 2011182849 A | * | 9/2011 |
| JP | 2011182849 A | | 9/2011 |
| JP | 2012203572 A | | 10/2012 |
| JP | 2015142690 A | | 8/2015 |

OTHER PUBLICATIONS

Written Opinion of the International Searching Authority issued in corresponding international application No. PCT/JP2017/016220, dated Jul. 25, 2017.

* cited by examiner

| No. | Contents to be written |
|---|---|
| 1 | Model number |
| 2 | Shipping date |
| 3 | Date of last usage |
| 4 | Usage day count |
| 5 | Lubrication count |
| 6 | Sterilization count |
| 7 | Usage hours |
| 8 | Date and time of last repair |
| 9 | Storage location of the latest (or oldest) data |
| 10 | Date and time of last lubrication |
| 11 | Date and time of last sterilization |
| 12 | Repair count |
| 13 | Turbine cartridge replacement count |
| 14 | Date and time of last turbine cartridge replacement |

DENTAL INSTRUMENT HANGER

CROSS-REFERENCE TO RELATED APPLICATIONS

This application is a U.S. National Stage Application under 35 U.S.C. § 371 of International Application No. PCT/JP2017/016220, filed on 24 Apr. 2017, and published on 7 Dec. 2017, as WO 2017/208678 A1, which claims the benefit of priority to Japanese Patent Application No. JP 2016-110411, filed on 1 Jun. 2016. The content of each of the above referenced patent applications is incorporated herein by reference in its entirety for any purpose whatsoever.

TECHNICAL FIELD

The invention relates to a dental instrument hanger.

BACKGROUND ART

In a dental clinic, instruments may be interchanged or a handpiece at the front end of an instrument may be interchanged with another one, for instance, so as to be used in diagnosis, treatment, or cleaning of teeth. As an example, an air turbine handpiece of dental turbine handpieces has a shaving tool rotated at high speed by compressed air, while water being injected, to shave a tooth. A micromotor handpiece also has a shaving tool rotated at high speed by an electric motor, while water being injected, to shave a tooth.

In order to appropriately manage maintenance of such a handpiece, a dental care system has been proposed that is capable of identifying only the instrument in use and acquiring its usage time (see Japanese Patent Application Publication No. 2015-142690A). In the dental care system disclosed in Japanese Patent Application Publication No. 2015-142690A, a wireless tag is attached to every instrument and a gate sensor is provided outside a hanger that hangs instruments before use. Arrangement is made such that when an instrument displaced from the hanger goes through the gate sensor, the wireless tag attached to the instrument transmits and receives information to and from the gate sensor.

SUMMARY OF THE INVENTION

Problems to be Solved

There is room for improvement in a conventional method of using a wireless tag to obtain usage time of an instrument. For instance, if a wireless tag attached to an instrument goes through the gate sensor in a too short time or goes out of the sensing area of a gate sensor, at the time of the instrument being displaced from a hanger, identification failure may possibly occur.

The present invention is therefore intended to provide a dental instrument hanger that is capable of solving the above-mentioned problems to reduce identification failure at the time of detecting an instrument being used.

Solution to Problem

In order to solve the above-mentioned problems, a dental instrument hanger according to the present invention includes: a hanger unit that displaceably houses instruments for dental use; a reading means that has its body, or an antenna connected to the body, arranged in the hanger unit to read identification information from a wireless tag, in a state that an instrument having the wireless tag preliminarily attached thereto is placed in the hanger unit; an identification information storage that stores in a database, for each reading history, the identification information of every wireless tag in the hanger unit, which is read by the reading means; a reading history detector that, in response to a driving instruction being inputted from outside for driving an instrument displaced from the hanger unit, detects with reference to the identification information storage the latest reading history and a reading history which had been read before the instrument displaced from the hanger unit has been displaced, for the identification information of every wireless tag; an identification information specifier that determines a difference between the two reading histories detected by the reading history detector to specify the difference as identification information of a wireless tag attached to the instrument which has been instructed to drive; and a usage information generator that generates usage information to specify that an instrument, to which the wireless tag identified by the specified identification information is attached, is used.

According to such a configuration, the dental instrument hanger is provided in the hanger unit with the body of the reading means or the antenna connected to the body. Then, the reading means reads the identification information from the wireless tag attached to the instrument, in a state that the instrument is placed in the hanger unit. This ensures a sufficient time for the reading means to read information from the wireless tag to reduce possibility of identification failure. In addition, identification information specific to the instrument is preliminarily perceived before the instrument is displaced from the hanger unit. The dental instrument hanger stores the identification information of the wireless tags in the identification information storage for every reading history, and then is capable of perceiving the identification information specific to the wireless tag attached to the instrument displaced from the hanger unit. In addition, the dental instrument hanger, in response to the driving instruction being inputted, generates usage information to specify that the instrument which has been instructed to drive is used, based on the difference between the latest reading history and the reading history before the instrument has been displaced from the hanger unit. This allows for distinguishing driving instruments from replacing instruments with respect to the instrument displaced from the hanger unit.

In addition, the dental instrument hanger according to the present invention is preferably configured so that the usage information generator extracts from a driving circuit, which drives the instrument, driving information of the instrument to which the wireless tag identified by the specified identification information is attached, to generate the cumulative usage time of the instrument from the extracted driving information. Such a configuration allows the dental instrument hanger to generate the cumulative usage time of the instrument and thus to record this cumulative usage time so as to be used for maintaining individual instruments.

Further, the dental instrument hanger according to the present invention may be configured so that the hanger unit includes: holders that individually house the instruments; and hanger sensors that detect, for the respective holders, the instruments being displaced or placed, wherein the reading means reads the identification information from the wireless tag every time the hanger sensor detecting the instrument being displaced or placed. Such a configuration allows the reading means to be activated only at a time of a hanger sensor arranged for every holder in the hanger unit detecting that the corresponding instrument is displaced or placed, and thus to save power.

Still further, the dental instrument hanger according to the present invention may be configured so that the hanger unit includes holders that individually house the instruments, wherein the reading means periodically reads the identification information from the wireless tags attached to the instruments which are placed in the holders. Such a configuration allows the reading means to be activated periodically, e.g., every one second, to readily determine a difference between the reading histories before and after an instrument being displaced from the hanger unit.

Still further, the dental instrument hanger according to the present invention may be configured so that the antenna of the reading means has a monitoring area to cover all the holders. Such a configuration allows the dental instrument hanger to have only a single large antenna arranged for the reading means, to reduce manufacturing costs.

Still further, the dental instrument hanger according to the present invention, when one large antenna is provided for the reading means, may include a position detection sensor that detects positions of the wireless tags attached to the instruments which are placed in the holders. Such a configuration allows the hanger sensors for the respective holders, which detect the instruments being displaced or placed, to be eliminated and then substitutes the function of the hanger sensors. Eliminating the hanger sensors reduces corresponding costs.

Still further, the dental instrument hanger according to the present invention may be configured so that the reading means or the antennas therefor are arranged for the respective holders. Such a configuration allows for using an HF (High Frequency) band antenna having small power, because the communication distance between the reading means or the antenna therefor and the wireless tag can be short. The configuration also allows the hanger sensors for the respective holders, which detect the instrument being displaced or placed, to be eliminated and then substitutes the function of the hanger sensors.

Still further, the dental instrument hanger according to the present invention, having the configuration such that the reading means or the antennas therefor are arranged for the respective holders, may be configured so that the reading means or the antennas therefor each read the identification information from the wireless tag attached to a handpiece of the instrument which is placed in the holder, and also each read the identification information from a second wireless tag attached to either an end of a hose connected to the handpiece via a connector or the connector. Such a configuration, on the condition that the hanger sensors are eliminated, substitutes the function of the hanger sensors, even when the connector and hose are hung in the holder in a state that the handpiece of the instrument is not mounted.

Still further, the dental instrument hanger according to the present invention may be configured so that one or more reading means or antennas therefor each read the identification information from the wireless tag attached to a tool for shaving or grinding a tooth, which is detachably mounted on a handpiece of the instrument which is placed in the hanger unit. Such a configuration allows for readily keeping information for managing the lifetime, timing of replacing parts, and routine maintenance from the accurate usage information obtained, even for a tool for shaving or grinding a tooth detachably mounted on the handpiece.

Still further, the dental instrument hanger according to the present invention may be configured so that one or more reading means or antennas therefor each read the identification information from the wireless tag attached to a cartridge stored within the head of a dental turbine handpiece of the instrument which is placed in the hanger unit. Such a configuration allows for readily keeping information for managing the lifetime, timing of replacing parts, and routine maintenance from the accurate usage information obtained, even for a cartridge stored within the head of a dental turbine handpiece.

Still further, the dental instrument hanger according to the present invention may be configures so that the reading means writes the usage information in the wireless tag attached to the instrument for which the usage information is generated. Such a configuration allows the dental instrument hanger, when reading recorded information from a wireless tag attached to an instrument, to read historical usage information generated up until the last event, in addition to the identification information of the instrument.

Still further, the dental instrument hanger according to the present invention may be configured to include a communicator that transmits and receives information inclusive of the usage information to and from an information processing device via a communication network. Such a configuration allows for connecting to an information processing device of a manufacturer, the cloud, or the like, for example, via a communication network to notify timing of replacing an instrument or an accessory thereof, or to automatically order such one.

Advantageous Effects of the Invention

The dental instrument hanger according to the present invention reduces identification failure at a time of detecting an instrument being used. Accordingly, accurate usage information is obtained to readily keep information for managing the lifetime, timing for replacing parts, and maintenance such as routine ones of the individual instruments. As a result, the necessity of maintenance is readily determined for individual instruments.

DETAILED DESCRIPTION OF EMBODIMENTS

Hereinafter, a description will be given in detail of embodiments of the present invention, with reference to the drawings.

First Embodiment

<Configuration of Dental Instrument Hanger>

Figure 1:
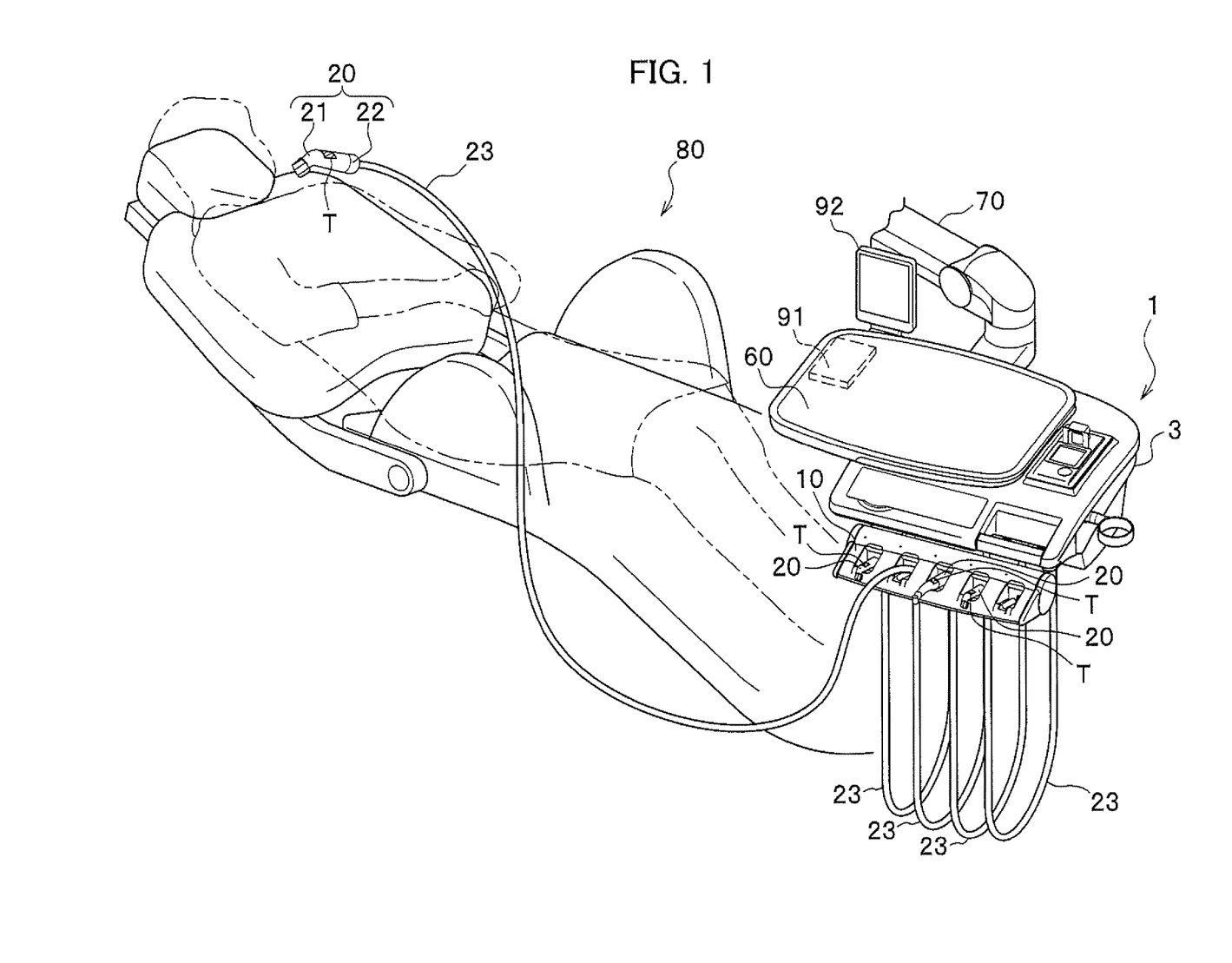
FIG. 1 is a diagram showing a dental instrument hanger according to a first embodiment of the present invention.

As shown in FIG. 1, a dental instrument hanger 1 includes a unit body 3 and a hanger unit 10 provided in the unit body 3. In this example, the dental instrument hanger 1 is supported by an arm unit 70. Note that the arm unit 70 is connected to a base of a patient chair 80 and other dental treatment facilities, although a portion of the arm unit 70 closer to the base end is not illustrated. Here, dental treatment equipment includes such as an automatic water faucet, a spittoon, a shadowless lamp, and a vacuum system, but those are not illustrated nor described.

In addition, the dental instrument hanger 1 usually includes an instrument hanger for a doctor and an instrument hanger for an assistant, but in the present embodiment, an instrument hanger for a doctor will be described as an example. Additionally, a description will be given in the present embodiment of the dental instrument hanger 1 supported by the arm unit 70, but the present invention is not limited to this type, and various types such as one installed in a stand or the like can be implemented, depending on application.

Figure 2:
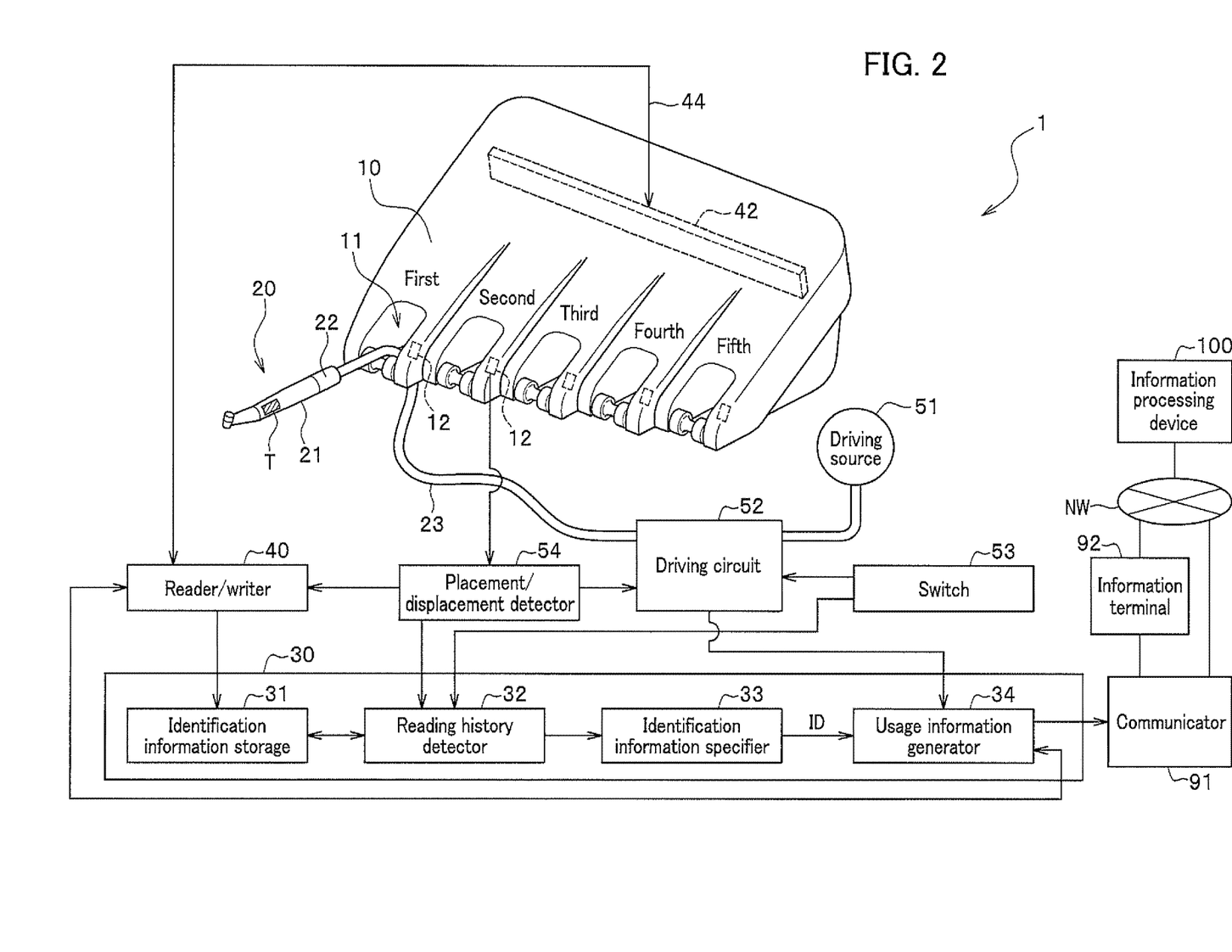
FIG. 2 is a block diagram schematically showing the dental instrument hanger according to the first embodiment of the present invention.

The hanger unit 10 displaceably houses dental instruments 20. As shown in FIG. 2, the hanger unit 10 has holders 11 which individually house the instruments 20 therein, respectively. In FIG. 2, the five holders 11 are shown as the first, second, - - -, fifth, from left to right, for distinguishing one from another. As shown in FIG. 2, the hanger unit 10 includes a hanger sensor 12 and a reader/writer (also referred to as a reading means) 40. In addition, a placement/displacement detector 54, a driving circuit 52, and a controller 30 are built in the unit body 3 (FIG. 1). Hereinbelow, the respective parts will be described.

<<Hanger Sensor>>

The hanger sensor 12 is provided at a portion of the hanger unit 10 where the instrument 20 is placed. The hanger sensor 12 detects the instrument 20 being displaced or placed for each holder 11 of the hanger unit 10. In this example, the first to fifth hanger sensors 12 are provided for the corresponding first to fifth holders 11. The hanger sensor 12 includes a reflective or transmissive optical sensor, for example. The hanger sensor 12, in a case of including a reflective optical sensor, detects that the instrument 20 is placed, if the optical path of light irradiated in the holder 11 is blocked by the instrument 20 and reflected light is received from the instrument 20. In contrast, the hanger sensor 12 detects that the instrument 20 has been displaced from the hanger unit 10, if reflected light is not received.

Alternatively, the hanger sensor 12, in a case of including a transmissive optical sensor, detects that the instrument 20 has been displaced from the hanger portion 10, if the light irradiated in the holder 11 is received. In contrast, the hanger sensor 12 detects that the instrument 20 is placed, if the optical path of light irradiated in the holder 11 is blocked by the instrument 20 and the hanger sensor 12 fails to receive light. Note that the hanger sensor 12 may include a magnetic sensor, or may include a contact sensor.

<<Reader/Writer>>

The reader/writer (or reading means) 40 reads information such as identification information from a wireless tag T in a state that the instrument 20 having the wireless tag T preliminarily attached thereto is placed in the hanger unit 10. In the present embodiment, the reader/writer 40 also writes predetermined information into the wireless tag T. The reader/writer 40 is assumed to be an RFID (Radio Frequency Identification) reader/writer. The reader/writer 40 includes an antenna 42 connected to the reader/writer via a lead wire 44, and this antenna 42 is disposed in the hanger unit 10. In this manner, the antenna 42 detects, with good directivity, the wireless tag T attached to the instrument 20 which is placed in the hanger unit 10, and the reader/writer reads the identification information.

In the present embodiment, the antenna 42 has a monitoring area covering all the holders 11. That is, the antenna 42 is a single large antenna and is built in the hanger unit 10 so as to cover all the holders 11. In addition, in the present embodiment, the antenna 42 of the reader/writer 40 communicates with the wireless tag T, every time the hanger sensor 12 detects the instrument 20 being displaced or placed, for the reader/writer 40 to read information from the wireless tag T. Note that the antenna 42 also communicates with the wireless tag T, when the main power is turned on.

<<Placement/Displacement Detector>>

The placement/displacement detector 54 detects that the instrument 20 is being displaced from the hanger unit 10 and that the instrument 20 is being placed in the hanger unit 10. The placement/displacement detector 54 controls the driving circuit 52 so as to drive only one instrument 20 with priority given to the one which has been displaced earlier. The placement/displacement detector 54 is provided in a general dental unit. The placement/displacement detector 54 includes a detection circuit that detects the instrument 20 being placed or displaced in accordance with a signal from the hanger sensor 12, and also includes an electric circuit such as a latch circuit that latches only detection information corresponding to the instrument 20 which has been displaced first.

The placement/displacement detector 54 uses pieces of information from the respective hanger sensors 12 to identify the holder 11 of the hanger unit 10 from which the instrument 20 actually in use by the operator has been displaced. Upon detecting the instrument 20 being placed or displaced, the placement/displacement detector 54 outputs a signal for activating the reader/writer 40 to the reader/writer 40. Note that in the present embodiment, in order to specify the holder 11 of the hanger unit 10 from which the instrument 20 has been displaced, the placement/displacement detector 54 notifies a reading history detector 32 of the instrument 20 being placed or displaced.

<<Driving Circuit>>

The driving circuit 52 is a well-known means for driving the instrument 20 and includes an electric circuit, a switching valve, and the like. The driving circuit 52 also includes a power supply circuit (power for micromotor operation, illumination, and warming), an air circuit (pressurized air for driving a turbine, and chip air for generating mist), a water supply circuit, and the like.

The water supply circuit, for example, is a circuit common to the instruments 20 and is connected so as to be available to only one instrument 20 in use. Here, for the purpose of illustration, driving circuits individually driving the instruments 20 are collectively referred to as the driving circuit 52. The driving circuit 52 operates in response to a driving instruction being inputted to drive the instrument 20 which is displaced from the hanger unit 10. This driving instruction is inputted to the driving circuit 52 by a switch 53. The switch 53 is a switch common to the instruments 20, and is, for example, a foot switch which is pushed with a foot to operate. The driving circuit 52 is connected to an external driving source 51. In FIG. 2, the driving source 51 collectively and schematically shows a power supply, an air source, a water supply source, and the like.

<<Instrument>>

The instrument 20 includes, for example, a handpiece 21 and a connector 22. A hose 23 is connected to the connector 22, and the hose 23 is connected to the driving source 51 via the driving circuit 52. The handpiece 21 is detachable from the connector 22, and has a wireless tag T attached thereto. Note that the handpiece 21 may be connected to the hose 23 so as not to be detached, depending on the type of the instrument.

<<Wireless Tag>>

The wireless tag T can have information read therefrom or written therein by the reader/writer 40 through non-contact communication. The wireless tag T is, for example, an RFID tag. At least specific ID (identification information) of the wireless tag T is preliminarily written in the wireless tag T. This identification information may be used as identification information for identifying the instrument 20 to which the wireless tag T is attached. Such a wireless tag T can be selected from various products which are commercially available, such as small products in a length of 1 cm or less and those for medical applications, and a small tag in a length of about several millimeters is preferably used. A commercially available product, for example, secures a storage capacity for storing its specific ID (e.g., 16 bytes) and a storage capacity for read/write operation (e.g., 112 bytes).

<<Controller>>

The controller 30 includes an identification information storage 31, a reading history detector 32, an identification information specifier 33, and a usage information generator 34. Note that the controller 30 includes such as a CPU (Central Processing Unit), a RAM (Random Access Memory), and a ROM (Read Only Memory).

<<Identification Information Storage>>

Figure 3:
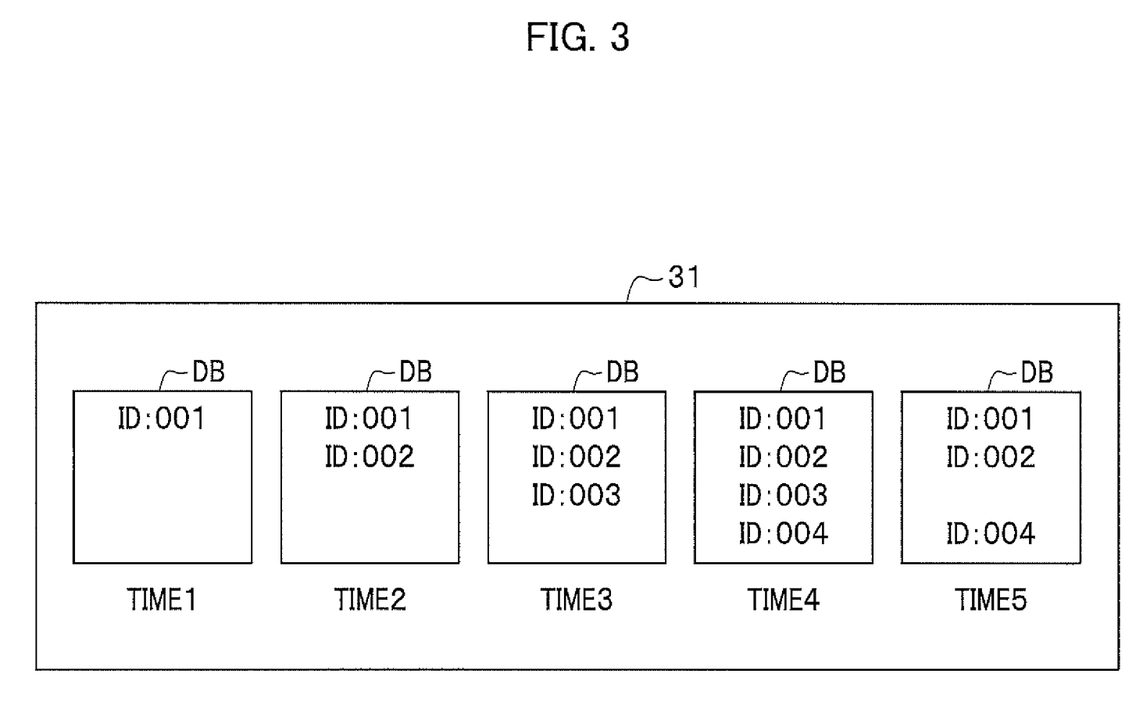
FIG. 3 is a schematic diagram showing example reading histories on identification information of an instrument.

The identification information storage 31 stores in a database, for each reading history, the identification information of every wireless tag T in the hanger unit 10, which is read by the reader/writer 40, and is configured with a generic memory or the like, for example. FIG. 3 is a diagram schematically showing an example of how the identification information is stored in the identification information storage 31. In the example in FIG. 3, reading-history databases DB are arranged in order of time, with an oldest-reading-history database DB on the leftmost side.

In this example, nothing was placed in the hanger unit 10. Then, at TIME1, the first instrument 20 was placed in the first holder 11, for instance, and identification information (hereinafter, simply referred to as ID) of 001 was read from the wireless tag T attached to the first instrument 20. After that, the instrument 20, to which the wireless tag T having ID of 001 is attached, had still been placed in the holder 11 of the hanger unit 10. In this state, at TIME2, the second instrument 20 was subsequently placed and ID of 002 was read from the wireless tag T attached to the second instrument 20 and stored together with ID of 001.

Similarly, at TIME3, the third instrument 20 was placed and newly read ID of 003 was additionally stored. Further, at TIME4, the fourth instrument 20 was placed and newly read ID of 004 was additionally stored. At TIME5, the instrument 20, to which the wireless tag T having ID of 003 is attached, was displaced from the hanger unit 10 and the reading-history database DB reflecting this was stored.

Note that the identification information storage 31 may have deletion executed such that DBs beginning with chronologically oldest one are deleted so as to keep only a predetermined number of relatively newer DBs, for example. In addition, when information other than the identification information is read from the wireless tag T by the reader/writer 40, such information may be stored in the identification information storage 31.

<<Reading History Detector>>

Once a driving instruction to drive the instrument 20 is inputted, the reading history detector 32 refers to the identification information storage 31 to detect, for the identification information of every wireless tag T, the latest reading history and a reading history before the instrument 20 displaced from the hanger unit 10 had been displaced from the hanger unit 10.

In this embodiment, the reader/writer 40 is directed to read information from the wireless tag T every time the hanger sensor 12 detects the instrument 20 being displaced or placed, as described above. Therefore, when the instrument 20 is displaced from the hanger unit 10, the reader/writer 40 reads the ID from the wireless tag T attached to every instrument 20 which is placed in the hanger unit 10 at that time. All the IDs read at this time constitute the latest reading history at the time of the driving instruction to drive the specified instrument 20 being inputted.

Additionally, the reading history before the instrument 20 had been displaced from the hanger unit 10 is a reading history including other ID in addition to all the IDs included in the latest reading history. Therefore, the reading history detector 32 sorts the reading histories stored in the identification information storage 31 in the order from latest to oldest, for instance, to search for a reading history having one more ID than the latest reading history. In this manner, the reading history detector 32 detects the reading history before the instrument 20 had been displaced from the hanger unit 10.

Specifically, in the example in FIG. 3, at the time when the four instruments 20 were placed in the hanger unit 10 (TIME4), the IDs read from the respective wireless tags T attached to all the instruments 20 were 001, 002, 003, and 004. The number of IDs in this reading history is four. With this assumption, the IDs read at the time when the instrument 20 having ID of 003 was displaced from the hanger unit 10 (TIME 5) were 001, 002, and 004. This is the latest reading history to include three IDs. Therefore, once a driving instruction to drive the instrument 20 is inputted in this case, the reading history detector 32 detects the reading history at the time the instrument 20 being displaced (TIME5) and the reading history at the time the number of IDs being four (TIME4). The reading history detector 32 outputs the two detected reading histories to the identification information specifier 33.

Note that in the present embodiment, the reading history detector 32 is configured to detect the reading history regardless of whether or not a driving instruction has been inputted, once a notification of the instrument 20 being placed or displaced is received from the placement/displacement detector 54. Therefore, the ID of the wireless tag T, which is attached to the instrument 20 being displaced from the hanger unit 10, can also be specified at the time of replacing the instrument 20.

<<Identification Information Specifier>>

The identification information specifier 33 determines a difference between the two reading histories detected by the reading history detector 32, to specify the difference as the identification information (ID) of the wireless tag T attached to the instrument 20 which has been instructed to drive. In the example of FIG. 3, the identification information specifier 33 specifies the ID of 003 as the difference between the reading history at the time of the instrument 20 being displaced (TIME5) and the reading history at the time of the number of the IDs being four (TIME4). In this manner, it is specified that the instrument 20 to which the wireless tag T having ID of 003 is attached was displaced from the hanger unit 10 and then driven. That is, the identification information specifier 33, based on the information read by the reader/writer 40, specifies the identification information of the instrument 20 which has been displaced from the hanger unit 10 and is being driven. The identification information specifier 33 outputs the identification information (ID) of the wireless tag T attached to the driven instrument 20 to the usage information generator 34.

<<Usage Information Generator>>

The usage information generator 34 generates usage information to specify that the instrument 20, to which the wireless tag T identified by the identification information (ID) specified by the identification information specifier 33 is attached, is used. The usage information includes date (year, month, and day) when the instrument 20 having the wireless tag T attached thereto is used, usage time of day, the number of days used, and the like, for example.

In the present embodiment, the usage information generator 34 extracts, from the driving circuit 52 that drives the instrument 20, driving information of the instrument 20 to which the wireless tag T having the ID specified by the identification information specifier 33 is attached. The usage information generator 34 generates cumulative usage time of the instrument 20 on the basis of the extracted driving information. Here, the cumulative usage time of the instrument is the driving time of the instrument. Normally, the operator uses the instrument 20 while switching on and off the switch 53. The cumulative usage time is accumulated time of the operator pushing the switch 53 to actually drive the instrument 20 (ON time), in the time information of the switch 53 being switched on and off.

In a case where the instrument 20 is an air turbine handpiece, for instance, the extracted driving information gives time information of the compressed air being switched on and off while the operator holds the handpiece 21. More specifically, information is obtained as cumulative usage time that the turbine blades (impellers) have rotated for 3 minutes, for example. Also obtained includes the length of time of water being injected to a shaving bur or an affected area.

In the present embodiment, the reader/writer 40 writes the usage information into the wireless tag T attached to the instrument for which the usage information has been generated. For this purpose, the reader/writer 40 is thus configured to notify the usage information generator 34 of the ID, when the ID is read from the wireless tag T, to request for the usage information. Then, the usage information generator 34 determines whether usage information has already been generated for the same ID as the ID in the request, and notifies the reader/writer 40 of corresponding usage information, if any.

Note that the usage information generator 34 may notify the reader/writer 40 of the usage information together with the ID, every time it generates the usage information, instead of the reader/writer 40 requesting for the usage information. In this case, if the ID read from the wireless tag T is the same as the ID notified by the usage information generator 34, the reader/writer 40 may write the notified usage information into the wireless tag T.

Information about the instrument 20 to be read and written for management includes, other than the usage information, information indicating such as the type of an instrument, maintenance information to be required in association with usage, and the like. For example, a handpiece needs to be autoclaved (sterilization) and periodically lubricated at the rotational bearing for maintenance, and these pieces of maintenance information may also be written. Also, information about a cartridge may be written, considering that some turbine blades (impellers) are provided in the form of a cartridge.

Figure 4:
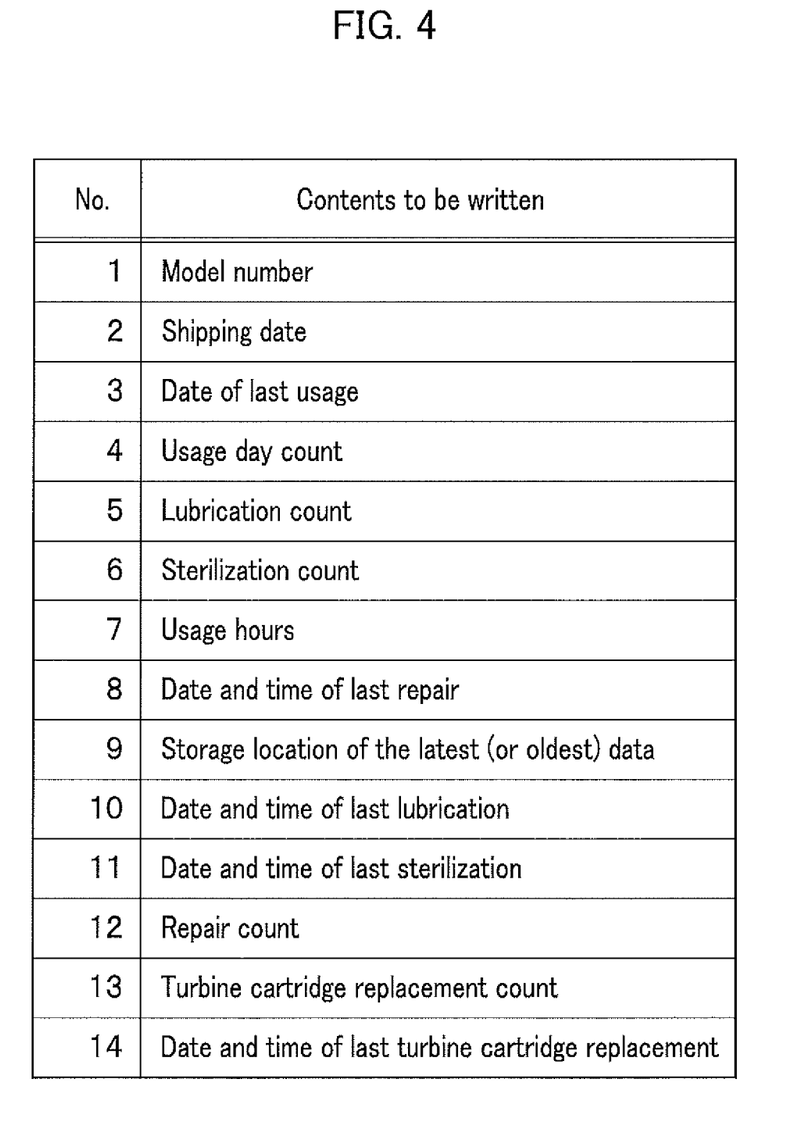
FIG. 4 is a schematic diagram showing example contents to be written in a wireless tag.

Here, example pieces of information on an instrument are shown in FIG. 4 that are to be read and written for management. FIG. 4 shows, as example contents to be written into the wireless tag T, model number, shipping date, date of last usage, usage day count, lubrication count, sterilization count, usage hours, date and time of last repair, storage location of the latest (or oldest) data, date and time of last lubrication, date and time of last sterilization, repair count, turbine cartridge replacement count, and date and time of last turbine cartridge replacement.

Note that in FIG. 4, the model number is a collective name of information to identify the instrument itself (type, function, model number). Here, the type is classified, for example, as a turbine, a handpiece, a syringe, a scaler, or the like. Information to identify the function varies depending on the type of the instrument. For instance, if the type of the instrument is a turbine, the information to identify the function includes the number of revolutions, information on whether or not an LED for illumination is provided at the front end, and the like.

In addition, these pieces of information may not be written into the wireless tag T, and may instead be stored and managed in a storage means within the unit body 3 or a server on the communication network, with the reader/writer 40 knowing only the ID of the wireless tag T. The identification information storage 31 may be used as the storage means within the unit body 3.

Returning to FIG. 1, the configuration of the dental instrument hanger 1 will be further described. As shown in FIG. 1, a communicator 91 is built in a table 60 on the unit body 3, and an information terminal 92 is provided on the table 60.

<<Communicator>>

The communicator 91 transmits and receives information to and from the information terminal 92. Here, the information to be transmitted and received is information obtained from the wireless tag T, or the like. Under the control of the controller 30, the communicator 91 transmits information to the information terminal 92 by short-range wireless communication. The short-range wireless communication standard includes a wireless LAN (Local Area Network) such as Wi-Fi (registered trademark), Bluetooth (registered trademark), and ZigBee (registered trademark). The communicator 91 transmits and receives information to and from the information terminal 92 and an external device via a communication network. Note that the communicator 91 may transmit and receive information to and from an external device via a communication network such as the Internet, without any intervention by the information terminal 92.

<<Information Terminal>>

The information terminal 92 is a device capable of communicating through a communication network such as the Internet. As the information terminal 92, a smartphone or a tablet PC, which are commercially available, may be used, for example. The information terminal 92 also functions as a display to show the received information. This allows the staff of a dental clinic such as a doctor to confirm maintenance information and the like shown on the display of the information terminal 92.

<Operation of Dental Instrument Hanger>

Hereinbelow, a description will be given based on the assumption, as an example, that the four instruments 20 in total are preliminarily placed and ready in the first to fourth holders 11 of the hanger unit 10, before the main power of the dental instrument hanger 1 is turned on.

First, once the main power is turned on, the antenna 42 of the reader/writer 40 communicates with the respective wireless tags T attached to the four instruments 20. Then, the identification information storage 31 stores via the reader/writer 40 the identification information (ID) of the wireless tag T attached to every instrument 20 which is placed in the hanger unit 10. In this manner, the same IDs as the reading history at the time of TIME4 in FIG. 3, for example, are respectively stored, in the initial state after the main power has been turned on.

Thereafter, the antenna 42 of the reader/writer 40 communicates with the wireless tag T only when the hanger sensor 12 senses something. For example, once the instrument 20 is displaced from the third holder 3, the placement/displacement detector 54 detects that some instrument 20 having unknown ID has been displaced from the hanger unit 10 according to a signal from the third hanger sensor 12. Then, the placement/displacement detector 54 outputs a signal for activating the reader/writer 40 to the reader/writer 40. The antenna 42 of the reader/writer 40 communicates with the wireless tags T attached to the remaining three instruments 20 which are placed in the respective holders 11. As a result, the IDs read by the reader/writer 40 are newly stored in the identification information storage 31. In this manner, the same IDs as the reading history at the time of TIME5 in FIG. 3, for example, are respectively stored.

This allows the dental instrument hanger 1 to specify which instrument 20 has been displaced from the hanger unit 10 with respect to the state at the time of the main power having been turned on, based on the difference between the information of the reading history at this time and the information of the reading history at the time of the main power having been turned on. That is, the dental instrument hanger 1 is capable of specifying the ID of the wireless tag T attached to the displaced instrument 20. However, even if the instrument 20 is displaced from the hanger unit 10, the instrument 20 may not necessarily be driven by the switch 53. For example, the handpiece 21 at the front end of the instrument 20 may be replaced.

Note that following operation is possible to replace the handpiece 21, even when the required instruments 20 are preliminarily placed and ready in the hanger unit 10 before the main power being turned on. One assumed case is that an air turbine handpiece having the maximum rotation speed of 300 thousand revolutions per minute has been ready, for example, but an air turbine handpiece having a rotation speed of 400 thousand revolutions per minute is actually found to be required. If ID of 003 has been written in the wireless tag T attached to the handpiece 21 that needs to be replaced, for example, that ID is already read by the reader/writer 40 at the time of the main power being turned on. However, if ID of 005 is written in the wireless tag T attached to the replacing handpiece 21, initial setting is required to make the reader/writer 40 read ID of 005. Then, the instrument 20 is placed in the hanger unit 10 without being driven, after the handpiece 21 at the front end of the instrument 20, which has been displaced for replacement, is replaced. This causes the reader/writer 40 to read ID of 005 from the wireless tag T.

In contrast, in the case of driving the instrument 20 for diagnosis, treatment, or cleaning teeth, the operator displaces the instrument 20, to which the wireless tag T having ID of 003 is attached, from the third holder 11, for example, and then pushes the switch 53 to drive it. This activates the driving circuit 52. At this time, the reading history detector 32 refers to the identification information storage 31 to detect the latest reading history (e.g., the reading history at TIME5) and the reading history before this instrument 20 had been displaced from the hanger unit 10 (e.g., the reading history at TIME4), and outputs these to the identification information specifier 33. Then, the identification information specifier 33 determines from the difference between the two reading histories that the handpiece 21, to which the wireless tag T having ID of 003 is attached, has been used. Based on this, the usage information generator 34 generates usage information of the handpiece 21 (usage information of the instrument). At this time, the usage information generator 34 extracts the driving information from the driving circuit 52 to generate the cumulative usage time.

Once the used instrument 20 is placed back in the hanger unit 10, the antenna 42 of the reader/writer 40 communicates with the wireless tag T attached to every instrument 20 which is placed in the hanger unit 10. In addition, when the ID (e.g., "003") is read from the wireless tag T attached to the instrument 20 placed in the third holder 11, for example, the reader/writer 40 notifies the usage information generator 34 of the ID to request for usage information. Then, the usage information generator 34 notifies the reader/writer 40 of the usage information corresponding to the read ID. The reader/writer 40 then writes the notified usage information into the wireless tag T identified by the corresponding ID. This allows the antenna 42, when it communicates with the respective wireless tags T placed in the hanger unit 10 at the time of the reader/writer 40 being activated next time, to read the previous usage information and the like from the wireless tag T having ID of 003, for example. This information can also be shown on the display of the information terminal 92 via the communicator 91.

As described above, the dental instrument hanger 1 according to the present embodiment includes the antenna 42, which is connected to the reader/writer 40, in the hanger unit 10. Thus, the antenna 42 is capable of reading the IDs from the wireless tags T attached to the instruments 20, in a state that the instruments 20 are placed in the holders 11 of the hanger unit 10. This secures enough time for the reader/writer 40 to read information from the wireless tags T, to have less identification failure. Therefore, the usage information generator 34 accurately obtains the cumulative usage time of the individual instruments 20 through the information extracted from the driving circuit 52.

In addition, the dental instrument hanger 1 of the present embodiment is designed so that the reader/writer 40 reads information from the wireless tag T, every time the reader/writer 40 detects the instrument 20 being placed or displaced, to save power of the reader/writer 40. Further, the dental instrument hanger 1 of the present embodiment is configured to have one large antenna 42 so that the monitoring area of the antenna 42 covers all the holders 11, to have reduced manufacturing costs. However, the present invention is not limited to these embodiments, and can be implemented within a scope of its spirit being unchanged.

First Modification of First Embodiment

In the first embodiment, upon detecting the instrument 20 being placed or displaced based on a signal from the hanger sensor 12, the placement/displacement detector 54 transmits a signal for activating the reader/writer 40 to the reader/ writer 40. However, the reader/writer 40 may periodically read the identification information (ID) from the nearby wireless tag T. The present first modification is free from using the hanger sensor 12 and the placement/displacement detector 54 for activating the reader/writer 40. The first modification is then configured to exclude the hanger sensor 12 and the placement/displacement detector 54. Note that other parts are the same as those in FIG. 2, and therefore no drawing is provided for the first modification.

Here, the term "periodically" means that the time is predetermined and may be at the same interval of time (such as every second) or at different time intervals. In addition, the RFID technology requires about several milliseconds for communication between the antenna of the reader/writer and the IC tag, to allow the reader/writer 40 to read the IDs several times, several tens of times, or several hundred times per second. That is, the first modification is designed so that the reader/writer 40 periodically reads the IDs at a time interval of about 1 second or less, and then is safely said to utilize a technique of reading information all the time in a normal sense, as compared with the technique of reading information from the wireless tag T every time the instrument 20 is placed or displaced.

Further, the first modification is designed so that the reading history detector 32 periodically refers to the identification information storage 31 at a predetermined frequency, not only at the time of the driving instruction being inputted for driving the instrument 20, to detect the latest reading history for the identification information of every wireless tag T. It is assumed that the frequency of the reading history detector 32 referring to the identification information storage 31 is equal to the frequency of reading the wireless tag T by the reader/writer 40 or more, e.g. every second. Note that the upper limit may be a time interval that allows for sensing that the instrument 20 has been displaced from the hanger unit 10. More specifically, the reader/writer 40 may read the wireless tag T every 0.5 seconds, for instance, to store the reading history into the identification information storage 31, while the reading history detector 32 may refer to the identification information storage 31 every second.

The first modification is designed so that the antenna 42, if the wireless tag T is detected in the vicinity thereof, periodically communicates with the wireless tag T since the main power has been turned on. Then, the reader/writer 40 routes the identification information (ID) of the wireless tag T attached to every instrument 20 which is placed in the hanger unit 10, to the identification information storage 31 so as to be stored therein. In the example in FIG. 3, prior to the instrument 20 being displaced from the hanger unit 10, the same reading-history database as the one at the time of the four instruments 20 being placed in the hanger unit 10 (TIME4) will be stored every 0.5 seconds, for example.

Thereafter, when the instrument 20 is displaced from the hanger unit 10, the wireless tag T attached to the instrument 20 is moved out of the monitoring area of the antenna 42. In the example in FIG. 3, once the instrument 20 is displaced from the hanger unit 10, the same reading-history database as the one at the time of the three instruments 20 being placed in the hanger unit 10 (TIME5) will be stored every 0.5 seconds, for example.

Note that the reading history detector 32, if it periodically refers to the identification information storage 31, is capable of readily specifying the difference changing from the reading history at the time of TIME4 to the reading history at the time of TIME5 in the example in FIG. 3, even if a large amount of reading histories are stored in the identification information storage 31. For example, the reading history detector 32, if it refers to the identification information storage 31 every second, is capable of determining substantially the moment at which time the instrument 20 is displaced from the hanger unit 10. Therefore, the reading history detector 32 is capable of readily detecting the wireless tag T which has been moved out of the monitoring area of the antenna 42, that is, the ID which is missing from the database in the identification information storage 31.

Note that the operation of the present modification when the switch 53 is pushed is the same as that of the first embodiment. In the first modification, the hanger sensor 12 and the placement/displacement detector 54 are eliminated, and then the manufacturing cost is reduced by that amount.

Second Modification of First Embodiment

The first modification of the first embodiment may further include a position detection sensor that detects the position of the wireless tag T attached to the instrument 20 which is placed in the holder 11. The position detection sensor may be of any type, as long as it communicates with the wireless tag T to detect the position of the wireless tag T, so that a commercially available small antenna or the like may be used. Note that the position detection sensor is provided separately from the antenna 42.

The second modification is configured to include position detection sensors that are provided at predetermined positions in the hanger unit 10, respectively. The number of the position detection sensors may be smaller (e.g., four) than the number of all the holders 11 (e.g., five). The respective positions where the position detection sensors are arranged and the position information of the wireless tag T obtained from the position detection sensor may preliminarily be calibrated by the reader/writer 40, to allow for perceiving which wireless tag T is placed at which location in the hanger unit 10. Thus, according to the second modification, both pieces of information detected by the position detection sensors and pieces of information read by the reader/writer 40 from the wireless tags T are used to perceive the correspondence relationship between the holders 11 in the hanger unit 10 and the IDs of the wireless tags T attached to the instruments 20 which are placed in the respective holders 11.

Second Embodiment

Figure 5:
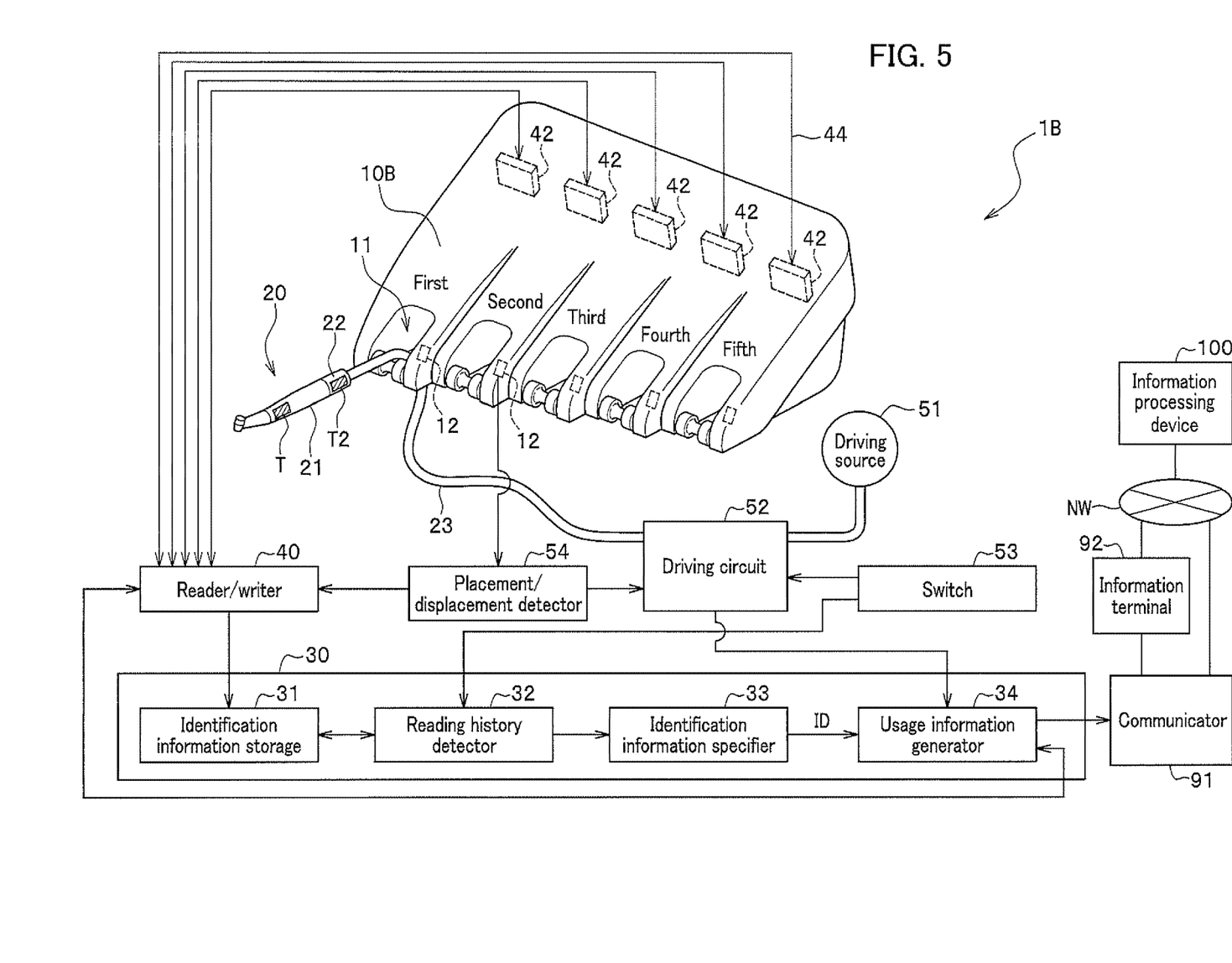
FIG. 5 is a block diagram schematically showing a dental instrument hanger according to a second embodiment of the present invention.

A description will be given of a dental instrument hanger 1B according to a second embodiment of the present invention, with reference to FIG. 5. Hereinbelow, the same components as those of the dental instrument hanger 1 according to the first embodiment are denoted by the same reference numerals, and descriptions thereof are omitted. The dental instrument hanger 1B includes antennas 42, each connected to the reader/writer 40, for the respective holders 11 in a hanger unit 10B. That is, the first holder 11 is provided for the first antenna 42, and the second holder 11 is provided for the second antenna 42. These small antennas 42 are built in the hanger unit 10B.

The present embodiment is designed to use the hanger sensor 12 and the antenna 42 for each holder 11 to specify the holder 11 in the hanger unit 10 from which the instrument 20 has been displaced. Then, the placement/displacement detector 54 is free from notifying the reading history detector 32 of the instrument 20 being placed or displaced.

Operation of the dental instrument hanger 1B will be described, assuming that the four instruments 20 in total are preliminarily placed and ready in the first to fourth holders 11 in the hanger unit 10B. Operation at the time of the main power being turned on is followed by, as in the first embodiment, the antenna 42 of the reader/writer 40 communicating with the wireless tag T only when the hanger sensor 12 has reacted. However, the antennas 42 that communicate with the wireless tags T are those corresponding to the holders 11 for which the reacted hanger sensors 12 are arranged.

When the instrument 20 is displaced from the third holder 11, for instance, the placement/displacement detector 54 outputs a signal for activating the reader/writer 40 to the reader/writer 40 in response to a signal from the third hanger sensor 12. In the state that the instrument 20 has been displaced from the third holder 11, the third antenna 42 fails to detect any nearby wireless tag T, but the remaining first, second and fourth antennas 42 detect nearby wireless tags T, respectively. As a result, the IDs read at the hanger unit 10B by the reader/writer 40 from the three wireless tags T, for example, are newly stored in the identification information storage 31. Thus, the same IDs as those in the reading history at TIME5 in FIG. 3, for example, are respectively stored. Note that operation when the switch 53 is pushed is the same as that in the first embodiment.

According to the dental instrument hanger 1B of the second embodiment, the communication distance between the antenna 42 and the wireless tag T can be short, to allow for using an HF band antenna having small power. In addition, according to the dental instrument hanger 1B of the second embodiment, power of the reader/writer 40 is saved as in the first embodiment.

First Modification of Second Embodiment

The second embodiment may also be modified so that every antenna 42 of the reader/writer 40 periodically reads identification information (ID) from the nearby wireless tag T. In this first modification, the hanger sensor 12 and the placement/displacement detector 54 are excluded. In addition, the reading history detector 32 periodically refers to the identification information storage 31 at a predetermined frequency, not only at the time of the driving instruction to drive the instrument 20 being inputted, to detect the latest reading history for the identification information of the wireless tag T attached to every instrument 20. Note that other parts are the same as those in FIG. 5, and therefore no drawing is provided for the present first modification.

Further, in the first modification, when the instrument 20 is displaced from the third holder 3, for instance, to the outside of the hanger unit 10, the wireless tag T attached to the corresponding instrument 20 is moved out of the monitoring area of the third antenna 42. This causes the ID of the moved wireless tag T to be missing from the database in the identification information storage 31, but the antennas 42 in the vicinity of the other holders 11 respectively continue to detect the nearby wireless tags T within the corresponding monitoring areas. Therefore, the identification information specifier 33 readily detects the wireless tag T moved out of the monitoring area of the third antenna 42, that is, the ID missing from the database in the identification information storage 31. Note that operation of the present modification when the switch 53 is pushed is the same as that of the first embodiment. In the first modification, the hanger sensor 12 and the placement/displacement detector 54 are eliminated, and then the manufacturing cost is reduced by that amount.

Second Modification of Second Embodiment

In the first modification of the second embodiment, the instrument 20 may have a second wireless tag T2 attached thereto together with the wireless tag T so that both tags are read by the reader/writer 40. Here, it is assumed as an example that the wireless tag T (hereinafter, referred to as a first wireless tag T for convenience) is attached to the handpiece 21 and the second wireless tag T2 is attached to the connector 22. Note that the second wireless tag T2 may be attached to an end of the hose 23 on the side closer to the connector 22.

The second wireless tag T2 is an RFID tag, for example, as with the first wireless tag T, and at least a specific ID (identification information) provided to the second wireless tag T2 is preliminarily written. This identification information may be used as identification information for identifying the connector 22 to which the second wireless tag T2 is attached. Here, the connector 22 and hose 23 of every instrument 20 are assumed to be used as being placed in a predetermined holder position in the hanger unit 10B. That is, the connector 22 and the hose 23, which are preliminarily determined to be placed in the first holder 11, are used so as not to be placed in the second holder 11, the third holder 11, or the like. In short, the identification information of the second wireless tag T2 is associated one-on-one with identification information for identifying the holder 11 of the hanger unit 10 (e.g., first, second, - - -, fifth). Note that the second wireless tag T2 may have identification information of the holders, such as first, second, - - -, fifth, written therein.

In a case where the handpiece 21 and the connector 22 are coupled to each other in the hanger unit 10B, the antenna 42 of the reader/writer 40 reads the identification information from the first wireless tag T attached to the handpiece 21 which is placed in the holder 11, and also reads the identification information from the second wireless tag T2 attached to the connector 22. In a case where the connector 22 is detached from the handpiece 21 and hung in the holder 11 in the hanger unit 10B, together with the hose 23, the antenna 42 reads identification information from the second wireless tag T2 attached to the connector 22. The antenna 42 for each holder 11, if it can read the identification information from the second wireless tag T2, obtains information that the connector 22, to which the second wireless tag T2 is attached, is hung in the corresponding holder 11 under monitoring, together with the hose 23. In contrast, the antenna 42, if it fails to read the identification information from the second wireless tag T2, obtains information that the connector 22 with the hose 23 is not hung in the corresponding holder 11. That is, in the case where the second wireless tag T2 is used, the antenna 42 for each holder 11 can substitute the function of the hanger sensor 12 to detect the instrument 20 being placed or displaced for each holder 11.

The second modification allows for substituting the function of the hanger sensor 12 even in a usage style of the connector 22 and hose 23 being hung in the holder 11, without the handpiece 21 being mounted on the instrument 20, in the state that the hanger sensor 12 is excluded as in the first modification of the second embodiment.

Other Modifications

In each of the above-described embodiments, the antenna 42 is arranged in the hanger unit 10 or 10B, but the reader/writer 40 may be arranged in the hanger unit 10 in place of the antenna 42. Alternatively, two or more reader/writers 40 may be arranged in the hanger unit 10.

In addition, the reader/writer 40 may be configured to read information from every wireless tag T and store it in the identification information storage 31, when the switch 53 is pushed, that is, when a driving instruction to drive the instrument 20 is inputted. In such a configuration, the reading history detector 32 detects, as the latest reading history, the reading history stored along with the switch 53 being turned on. Note that even if the switch 53 is switched on or off in order to drive or stop the displaced instrument 20, the latest reading history regarding the IDs detected every time when the switch is switched on remains unchanged, as long as said instrument 20 is displaced. Also in this case, the technique of detecting the reading history prior to the instrument 20, which is displaced from the hanger unit 10, having been displaced from the hanger unit 10 is the same as that described previously.

Further, as shown in FIG. 2, the communicator 91 may transmit and receive the usage information generated by the usage information generator 34 to and from an information processing device 100 via a communication network NW. In FIG. 2, the communication network NW includes a wired communication network using a wired LAN, a communication network such as a wireless LAN and Bluetooth (registered trademark), and a network such as the Internet, and is schematically shown. The information processing device 100 is configured with a generic personal computer (PC) or a portable terminal device such as a tablet PC, for example. The information processing device 100 may be a health-insurance-claims processing computer or a dental treatment facility having a network communication capability. The information processing device 100 is installed, for example, in a clinic room where the dental instrument hanger 1 is installed or other room in a dental clinic, in a manufacturer of an instrument or the like, in a call center for accepting a purchase order and a repair request of an instrument or the like, or on the cloud. With such a configuration, the dental instrument hanger 1 is connected to the information processing device 100 in the call center or on the cloud, for example, through the communication network NW, to transmit and receive the usage information generated by the usage information generator 34, and the like. This allows for such as managing maintenance of the instruments 20 and automatically ordering parts.

In each of the above-described embodiments, the wireless tag T is illustrated so as to be attached to the surface of the main body of the handpiece 21 in the instrument 20, but a part to which the wireless tag T is attached is not limited to said surface. A wireless tag may be attached, for example, to a shaving or grinding tool detachably attached to a handpiece 21 such as an air turbine, a micromotor, a scaler, or the like.

Here, a shaving or grinding tool is an accessory of a handpiece, and specifically includes those tools shown in the following 1), 2), and 3):
1) A dental bur that is attached to an air turbine or a micromotor to shave or grind a tooth or a restoration;
2) A reamer or file that is connected to a root canal enlarging motor to enlarge a root canal or to file a wall of a root canal; and
3) A tip that is attached to a scaler to remove dental calculus and dental plaque by ultrasonic vibration.

Figure 6:
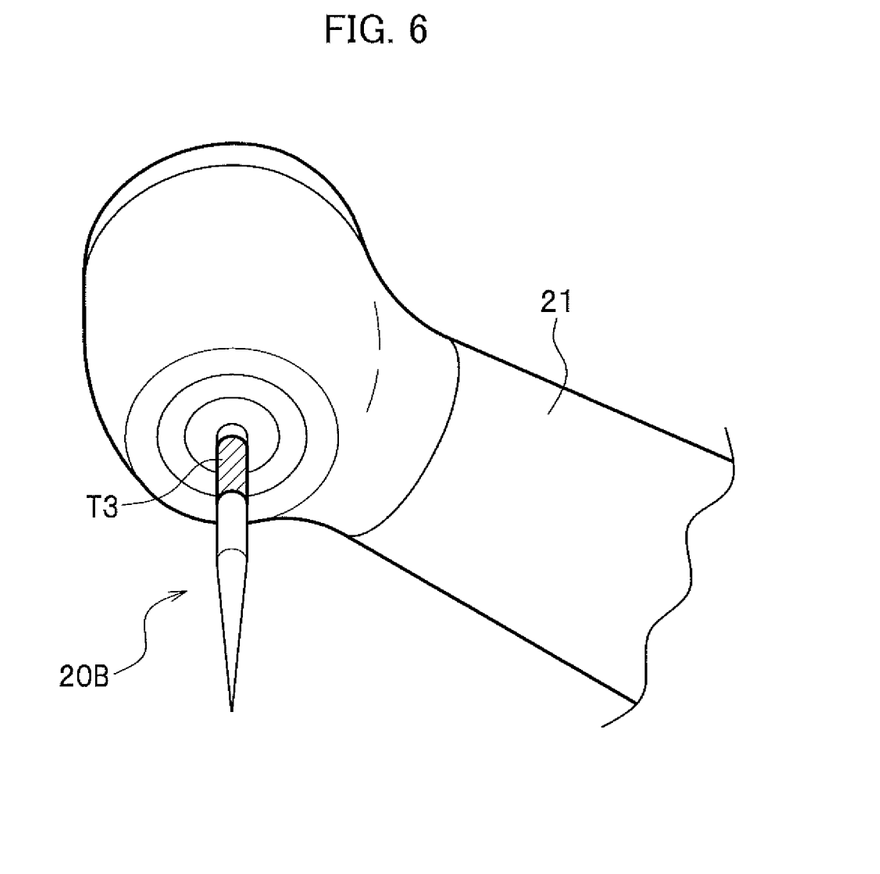
FIG. 6 is a perspective view of an example portion of an instrument to which a wireless tag is attached.

An example of a tool mounted on the handpiece 21 is shown in FIG. 6. FIG. 6 schematically illustrates a side of a head integrated with a main body of the handpiece 21 of an air turbine, for example, to be used to face the affected part. A tool 20B is assumed to be a shaving tool (dental bur) as an example. The tool 20B has a wireless tag attached thereto at a portion closer to the base end thereof. The wireless tag attached to the tool 20B will hereinafter be referred to as a third wireless tag T3 for convenience. The third wireless tag T3 is, for example, an RFID tag, as with the first wireless tag T, and is preliminarily written with at least a specific ID (identification information) provided to the third wireless tag T3. This identification information may be used as identification information to identify the tool 20B to which the third wireless tag T3 is attached. The third wireless tag T3 is used for the same purpose as the first wireless tag T, that is, for generating usage information of the tool 20B to which the third wireless tag T3 is attached.

In this way, the third wireless tag T3 is preliminarily attached to the tool 20B to allow the dental instrument hanger 1 to read identification information (ID) from the third wireless tag T3 by the reader/writer 40 or the antenna 42 in the hanger unit 10. This allows for readily keeping the information about the tool 20B, as with the handpiece 21, to manage the service life, timing of replacing parts, and routine maintenance. In addition, the dental instrument hanger 1 is connected to the information processing device 100 at the call center or on the cloud, for example, through the communication network NW, to transmit and receive the usage information of the tool 20B or the like for such as automatically ordering the tool 20B. Note that the third wireless tag T3 may be used together with the first wireless tag T and the second wireless tag T2.

Figure 7:
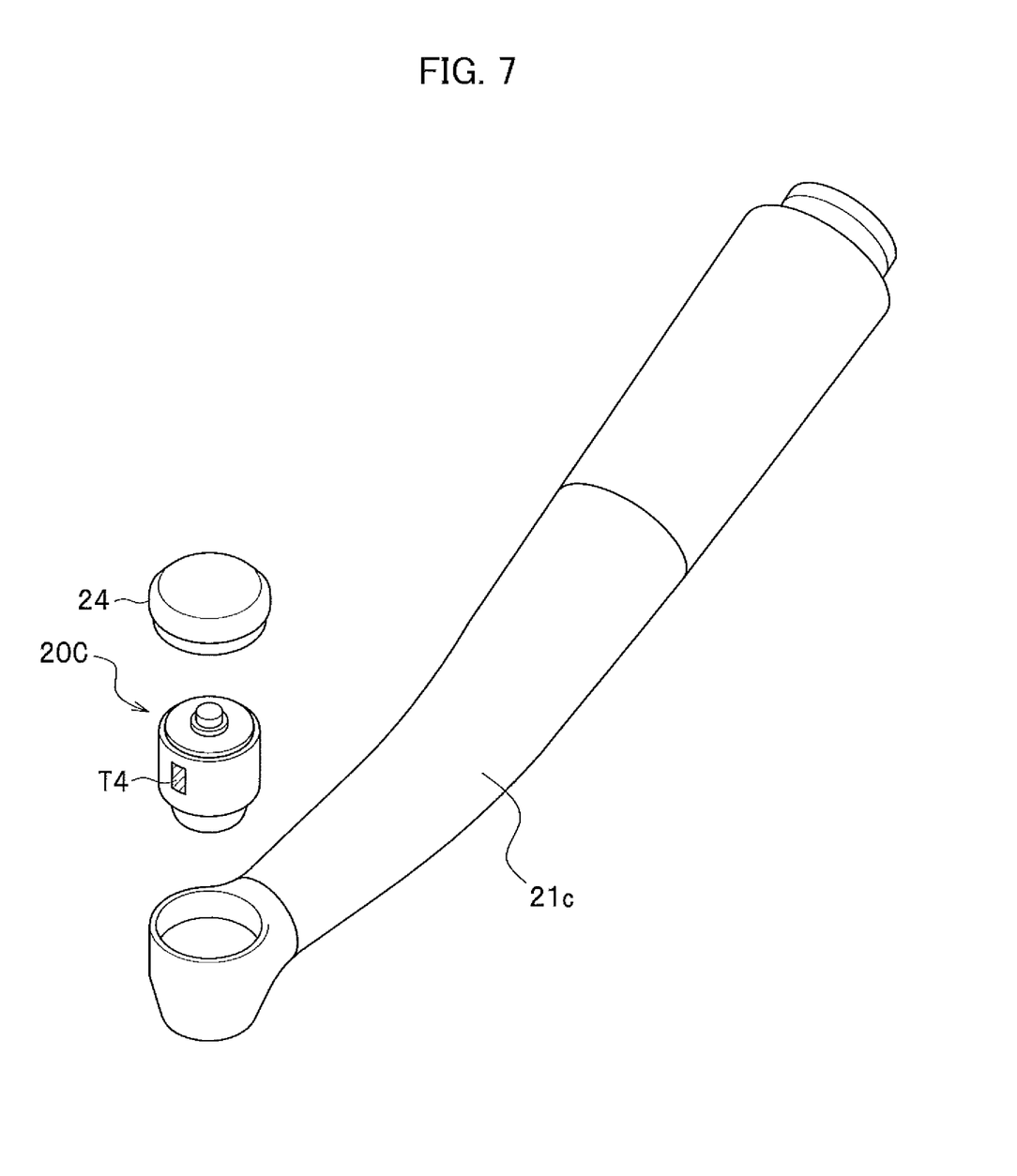
FIG. 7 is a perspective view of another example portion of an instrument to which a wireless tag is attached.

In addition, the wireless tag may be attached to a cartridge stored in a head of a dental turbine of a cartridge type, other than to the tool 20B. FIG. 7 schematically shows an exploded perspective view of a head integrated with the main body of a handpiece 21C in an air turbine of a cartridge type. The cartridge 20C has been known and is widely used in dental treatment. The cartridge 20C houses a structure in which blades are provided around a rotary shaft to which a shaving or grinding tool to be rotationally driven is mountable so as to be rotated by compressed air.

The cartridge 20C is detachably housed in the head of the handpiece 21C and covered by a lid 24. The cartridge 20C is replaceable, and at the time of replacement, a supplier cleans the air circuit inside the cartridge or does maintenance such as replacing an O-ring and a bearing which are components of the cartridge, for example. The cartridge 20C has a substantially cylindrical appearance, and has a wireless tag attached thereto at a predetermined position on its outer circumferential surface. The wireless tag attached to the cartridge 20C will hereinafter be referred to as a fourth wireless tag T4 for convenience. The fourth wireless tag T4 is, for example, an RFID tag, as with the first wireless tag T, and is preliminarily written with at least a specific ID (identification information) provided to the fourth wireless tag T4. This identification information may be used as identification information to identify the cartridge 20C to which the fourth wireless tag T4 is attached. The fourth wireless tag T4 is used for the same purpose as the first wireless tag T, that is, for generating usage information of the cartridge 20C to which the fourth wireless tag T4 is attached.

In this way, the fourth wireless tag T4 is preliminarily attached to the cartridge 20C to allow the dental instrument hanger 1 to read identification information (ID) from the fourth wireless tag T4 by the reader/writer 40 or the antenna 42 in the hanger unit 10. This allows for readily keeping the information about the cartridge 20C, as with the handpiece, to manage the service life, timing of replacing parts, and routine maintenance. In addition, the dental instrument hanger 1 is connected to the information processing device 100 at the call center or on the cloud, for example, through the communication network NW, to transmit and receive the usage information of the cartridge 20C or the like for such as informing timing of replacing the cartridge 20C and automatically ordering the cartridge 20C. Note that the fourth wireless tag T4 may be used together with the first wireless tag T, the second wireless tag T2, and the third wireless tag T3.

Note that when two or more wireless tags are used together for every instrument 20, pieces of identification information are simultaneously read by the reader/writer 40 from two or more wireless tags attached to every instrument placed in the hanger unit 10, and pieces of usage information corresponding to the respective wireless tags are individually generated. In addition, when two or more (e.g., two) wireless tags are used together, the reading history detector 32, once the reading histories stored in the identification information storing means 31 are sorted in the order from latest to oldest, may search for a reading history having a greater number of IDs than the latest reading history by the number of the wireless tags used together (e.g., two).

1, 1B Dental instrument hanger
10, 10B Hanger unit
11 Holder
12 Hanger sensor
20 Instrument
20B Shaving or grinding tool
20C Cartridge
21 Handpiece
21C Dental turbine handpiece
22 Connector
23 Hose
31 Identification information storage
32 Reading history detector
33 Identification information specifier
34 Usage information generator
40 Reader/writer (reading means)
42 Antenna
52 Driving circuit
91 Communicator
100 Information processing device
NW Communication network
T Wireless tag
T2 Second wireless tag
T3 Third wireless tag
T4 Fourth wireless tag

The invention claimed is:

1. A dental instrument hanger comprising:
a hanger unit configured to removably house one or more instruments for dental use, the one or more instruments each having a wireless tag attached thereto;
a reading means configured to read one or more pieces of identification information of the one or more instruments placed in the hanger unit from the one or more wireless tags at a predetermined timing, wherein the reading means or an antenna connected to the reading means is arranged in the hanger unit; and
a controller including:
an identification information storage configured to store the one or more pieces of identification information, as a database, for every reading history of the one or more wireless tags read by the reading means;
a reading history detector configured, in response to a driving instruction being inputted from outside of the hanger unit for driving one of the one or more instruments removed from the hanger unit, to detect a latest reading history and previous reading history from the identification information storage, the previous reading history being a reading history obtained prior to removing said one of the one or more instruments from the hanger unit;
an identification information specifier configured to determine a difference between the latest and previous reading histories, and use the difference to specify identification information of the wireless tag attached to said one of the one or more instruments; and
a usage information generator configured to generate usage information for said one of the one or more instruments.

2. The dental instrument hanger according to claim 1, wherein the usage information generator extracts driving information from a driving circuit, which drives said one of the one or more instruments, to generate a cumulative usage time of said one of the one or more instruments from the extracted driving information.

3. The dental instrument hanger according to claim 1, wherein the hanger unit includes: holders configured to individually house the instruments; and hanger sensors configured to detect, for the respective holders, the instruments being removed or placed,
wherein the reading means reads the identification information from the wireless tag every time the hanger sensor detecting the instrument being removed or placed.

4. The dental instrument hanger according to claim 1, wherein the hanger unit includes holders configured to individually house the instruments,
wherein the reading means periodically reads the identification information from the wireless tags attached to the instruments which are placed in the holders.

5. The dental instrument hanger according to claim 3, wherein the antenna has a monitoring area to cover all the holders.

6. The dental instrument hanger according to claim 4, wherein the antenna has a monitoring area to cover all the holders.

7. The dental instrument hanger according to claim 6, wherein the hanger unit further includes:
a position detection sensor configured to detect positions of the wireless tags attached to the instruments which are placed in the holders.

8. The dental instrument hanger according to claim 3, wherein either the reading means or the antennas is arranged for the respective holders.

9. The dental instrument hanger according to claim 4, wherein either the reading means or the antennas is arranged for the respective holders.

10. The dental instrument hanger according to claim 9, wherein either the reading means or the antennas therefor each read the identification information from the wireless tag attached to a handpiece of the instrument which is placed in the holder, and also each read the identification information from a second wireless tag attached to either an end of a hose connected to the handpiece via a connector or the connector.

11. The dental instrument hanger according to claim 1, wherein either one or more said reading means or antennas therefor each read the identification information from the wireless tag attached to a tool for shaving or grinding a tooth, which is detachably mounted on a handpiece of the instrument which is placed in the hanger unit.

12. The dental instrument hanger according to claim 1, wherein one or more said reading means or antenna therefor each read the identification information from the wireless tag attached to a cartridge stored within the head of a dental turbine handpiece of the instrument which is placed in the hanger unit.

13. The dental instrument hanger according to claim 1, wherein the reading means writes the usage information into the wireless tag attached to the instrument for which the usage information has been generated.

14. The dental instrument hanger according to claim 1, further comprising:
a communicator configured to transmit and receive information inclusive of the usage information to and from an information processing device via a communication network.

15. The dental instrument hanger according to claim 2, wherein the hanger unit includes: holders configured to individually house the instruments; and hanger sensors configured to detect, for the respective holders, the instruments being removed or placed,
wherein the reading means reads the one or more pieces of identification information from the one or more wireless tags every time one of the hanger sensors detecting the associated instrument being removed or placed.

16. The dental instrument hanger according to claim 2, wherein the hanger unit includes holders configured to individually house the instruments,
wherein the reading means periodically reads the one or more pieces of identification information from the one or more wireless tags attached to the respective instruments which are placed in the holders.

17. The dental instrument hanger according to claim 2, wherein one or more said reading means or antennas therefor each read the identification information from the wireless tag attached to a tool for shaving or grinding a tooth, which is detachably mounted on a handpiece of the instrument which is placed in the hanger unit.

18. The dental instrument hanger according to claim 2, wherein one or more said reading means or antenna therefor each read the identification information from the wireless tag attached to a cartridge stored within the head of a dental turbine handpiece of the instrument which is placed in the hanger unit.

19. The dental instrument hanger according to claim 2, wherein the reading means writes the usage information into the wireless tag attached to the instrument for which the usage information has been generated.

20. The dental instrument hanger according to claim 2, further comprising:
a communicator configured to transmit and receive information inclusive of the usage information to and from an information processing device via a communication network.

* * * * *